(12) United States Patent
Reeve et al.

(10) Patent No.: US 9,216,026 B2
(45) Date of Patent: *Dec. 22, 2015

(54) FEMORAL SIZING GUIDE

(75) Inventors: Michael Reeve, Beeston (GB); Michael Rock, Beeston (GB)

(73) Assignee: DEPUY (IRELAND), Cork (IE)

( * ) Notice: Subject to any disclaimer, the term of this patent is extended or adjusted under 35 U.S.C. 154(b) by 125 days.

This patent is subject to a terminal disclaimer.

(21) Appl. No.: 13/697,403

(22) PCT Filed: Mar. 23, 2011

(86) PCT No.: PCT/GB2011/050575
§ 371 (c)(1),
(2), (4) Date: Jan. 15, 2013

(87) PCT Pub. No.: WO2011/141722
PCT Pub. Date: Nov. 17, 2011

(65) Prior Publication Data
US 2014/0148811 A1    May 29, 2014

(30) Foreign Application Priority Data
May 11, 2010 (GB) .................................. 1007783.2

(51) Int. Cl.
*A61B 17/58* (2006.01)
*A61B 17/60* (2006.01)
(Continued)

(52) U.S. Cl.
CPC ........... *A61B 17/1764* (2013.01); *A61B 17/155* (2013.01); *A61B 2019/461* (2013.01);
(Continued)

(58) Field of Classification Search
CPC .. A61B 17/154; A61B 17/155; A61B 17/157; A61B 17/158; A61B 17/1764

USPC ................................................... 606/86 R–89
See application file for complete search history.

(56) References Cited

U.S. PATENT DOCUMENTS 4,703,751 A    11/1987    Pohl
5,364,401 A    11/1994    Ferrante
(Continued)

FOREIGN PATENT DOCUMENTS

EP        791334 A1    8/1997
FR        2813780 A1   3/2002
(Continued)

OTHER PUBLICATIONS

PCT International Search Report and Written Opinion PCT/GB2011/050575 dated May 26, 2011.
(Continued)

*Primary Examiner* — Kevin T Truong
*Assistant Examiner* — Si Ming Ku (57) ABSTRACT

A femoral sizing guide comprises a body, a superstructure and a stylus. The body has feet extending underneath and resting against posterior condylar surfaces of the femur and an extension component. The superstructure is slidable on the extension component and the extension component is rotatable with respect to the feet. The stylus may be coupled to the superstructure. The superstructure has a first guide hole defining a first alignment axis and the extension component has a second guide hole defining a second alignment axis. The distance between the first and second guide holes varies as the superstructure slides relative to the body. A method of locating an alignment axis on a resected femoral surface at a distal end of a femur which is transverse to the longitudinal axis of the femur using the femoral sizing guide is also disclosed.

18 Claims, 6 Drawing Sheets

(51) Int. Cl.
  *A61F 2/00* (2006.01)
  *A61B 17/17* (2006.01)
  *A61B 17/15* (2006.01)
  *A61B 19/00* (2006.01)
  *A61F 2/38* (2006.01)
  *A61F 2/30* (2006.01)
  *A61F 2/46* (2006.01)

(52) U.S. Cl.
  CPC ..... *A61F2/3859* (2013.01); *A61F 2002/30617* (2013.01); *A61F 2002/4658* (2013.01); *A61F 2250/0097* (2013.01)

(56) References Cited

U.S. PATENT DOCUMENTS

| | | | |
|---|---|---|---|
| 5,486,178 | A | 1/1996 | Hodge |
| 5,540,696 | A | 7/1996 | Booth, Jr. |
| 5,569,261 | A | 10/1996 | Marik |
| 5,688,279 | A | 11/1997 | McNulty |
| 5,688,280 | A | 11/1997 | Booth, Jr. |
| 6,013,081 | A | 1/2000 | Burkinshaw |
| 6,458,135 | B1 | 10/2002 | Harwin |
| 6,602,258 | B1 | 8/2003 | Katz |
| 7,451,550 | B2 * | 11/2008 | Dees, Jr. .......... 33/512 |
| 7,488,324 | B1 | 2/2009 | Metzger |
| 8,382,764 | B2 | 2/2013 | Dower |
| 2004/0220583 | A1 | 11/2004 | Pieczynski |
| 2006/0184173 | A1 | 8/2006 | Collazo |
| 2006/0241634 | A1 * | 10/2006 | Tuttle et al. ........ 606/86 |
| 2007/0173851 | A1 * | 7/2007 | McMillen et al. ..... 606/87 |
| 2007/0233140 | A1 * | 10/2007 | Metzger et al. ....... 606/88 |
| 2008/0161824 | A1 | 7/2008 | McMillen |
| 2009/0143783 | A1 * | 6/2009 | Dower ............ 606/88 |
| 2010/0286524 | A1 | 11/2010 | Daoura |
| 2011/0046685 | A1 | 2/2011 | Faure |

FOREIGN PATENT DOCUMENTS

| | | |
|---|---|---|
| JP | 09006066 A | 1/2009 |
| WO | WO 2006069336 A1 | 6/2006 |

OTHER PUBLICATIONS

UK Search Report GB1007783.2 dated Aug. 18, 2010.
The Concept of Personalization, Legend II Surgical Technique, The AMK Total Knee System Instrumentation, 20M0392, 0601-12, 1992 (31 Pages).
Legend II Surgical Technique, AMK Total Knee System Using AMK Legend II Instruments, 1M800, 0601-12-000 (Rev. 6) 1998 29 Pages.
PFC Sigma RP-F Specialist Instruments Surgical Technique, 9090-12-000 Version 2, 2004, 32 Pages.
Surgical Technique for Use With P.F.C. Knee Systems, Johnson & Johnson Orthopaedics, Primary Cruciate-Retaining Procedure, Specialist 2 Instruments, SP2-001, 1996, 61 Pages.
Surgical Technique for Use With P.F.C. Sigma Knee Systems, Primary Cruciate-Retaining and Cruciate Substituting Procedure, Specialist 2 Instruments, SP2-007 Rev. 4, 1998, 106 Pages.
Chinese Search Report for Application No. 201180023366.5, 13 Pages.
Japanese Search Report for Application No. 2013-509613, Date Drafted Oct. 31, 2014, 11 Pages.
Australian Search Report for Application No. 2011251778, Date of Issue Nov. 27, 2014, 4 Pages.
Australian Search Report for Application No. 2011251779, Date of Issue May 27, 2014, 3 Pages.
Japanese Search Report for Application No. 2013-509614, Date Drafted Dec. 5, 2014, 8 Pages.
PCT Int'l Search Report/Written Opinion PCT/GB2011/050582 Dated Jul. 27, 2011.
UK Search Report GB1007782.4 Dated Aug. 19, 2010.
UK Search Report for App. No. GB1119481.8 Dated Feb. 22, 2012.
PCT Search Report PCT/GB2012/052571 Dated Jan. 4, 2013.

* cited by examiner

FEMORAL SIZING GUIDE

CROSS REFERENCE TO RELATED APPLICATION

This application is a National Stage 35 U.S.C. 371 of International Patent Application PCT/GB2011/050575 filed Mar. 23, 2011.

BACKGROUND OF THE INVENTION

The present invention relates generally to femoral sizing guide. In particular, embodiments of the present invention relate to femoral sizing guides for accurately positioning a cutting block on a resected distal portion of a femur in order to locate cutting planes for preparing the end of the femur to receive a prosthetic implant. The present invention also relates to methods of using femoral sizing guides.

During the lifetime of a patient, it may be necessary to perform a joint replacement procedure on the patient as a result of, for example, disease or trauma. The joint replacement procedure, or joint arthroplasty, may involve the use of a prosthesis which is implanted into one of the patient's bones.

During performance of a joint replacement procedure, it is generally important to provide the orthopedic surgeon with a certain degree of flexibility in the selection of the correct size of prosthesis. In particular, the anatomy of the bone into which the prosthesis is to be implanted may vary somewhat from patient to patient. In order to implant a prosthetic joint, it is commonly necessary to prepare the bone to receive the prosthesis. For a prosthetic knee joint, both the distal femur and the proximal tibia may need to be accurately resected to shape the ends of the bones to receive the implants. For preparing the distal femur as a first preparatory step, a transverse surface is formed at the distal end of the femur by performing a first resection. This resection may be located using separate instruments, not described in detail here.

Femoral knee prostheses are typically provided in a range of standard sizes. Once selected, the femoral knee prosthesis must be located and oriented to provide appropriate rotational alignment. Correct selection of the size of prosthesis and correct positioning of the prosthesis relative to the natural bone is essential to ensure natural movement of the assembled joint. In particular, the implant must be positioned to provide an appropriate gap between the femur and the tibia when the knee is in extension and in flexion, and to ensure that the surrounding tissues are correctly balanced. It is known to set the rotation of the femoral prosthesis relative to Whiteside's line, which extends from the intercondylar notch to the patella groove. Alternatively, the rotation of the femoral prosthesis may be set relative to the transepicondylar axis, which connects the high points of the epicondyles. Further anatomical reference marks may also be used.

It is known to use a femoral sizing guide mounted on the resected distal femur surface to measure the size of the distal femur, and in particular the size of the condyles and to specify the required locations of guiding apertures into the femur to secure an appropriate cutting block to the femur to prepare the femur to receive the prosthesis. A surgical instrument set for performing a knee replacement procedure including a femoral sizing guide is marketed by DePuy Orthopedics, Inc. under the trade mark Sigma High Performance Instruments. The Sigma HP instrument set allows surgeons to perform total knee arthroplasty procedures under most surgical approaches.

The Sigma HP femoral sizing guide is used to determine the correct size for the femoral prosthesis and to position guide pins to support a cutting block on the distal end of the femur. A body portion of the femoral sizing guide is seated upon the resected femoral surface. Posterior feet extend from the body underneath the posterior condyles. The femoral sizing guide is correctly located when the posterior condylar surfaces rest upon the feet with Whiteside's line extending generally centrally through the sizing guide. When the feet are correctly located the body is can be secured to the bone with pins which extend into the bone through fixed position pin holes. A stylus is coupled to the body such that it can be raised and lowered and locked in position. The stylus tip extends over the anterior cortex of the distal femur. The stylus can also rotate about an axis extending generally parallel to the resected surface and can slide through the coupling to the body along the anterior cortex generally parallel to the longitudinal axis of the femur. The tip of the stylus is positioned upon the anterior cortex of the femur at the intended exit point of the anterior cut for the femoral prosthesis. The height of the stylus above the condylar feet can be read off a scale upon the body and indicates the size of the required prosthesis. A scale on the stylus indicates the exit point on the anterior cortex for each size of prosthesis. The chosen size of the femoral prosthesis determines the size of cutting block to be coupled to the distal transverse surface of the femur. The stylus position sliding through the sizing guide and the height of the stylus above the feet are set to the same value on the respective scales (corresponding to the size of the femoral prosthesis). When the tip of the stylus just contacts the anterior cortex as the stylus sweeps across the anterior cortex, the anterior part of the corresponding size of femoral prosthesis will terminate at the anterior surface of the bone without leaving a notch or an overhang.

BRIEF SUMMARY OF THE INVENTION

There are two alternative surgical approaches for positioning a femoral prosthesis using the Sigma HP instrument set. These are termed "posterior up" and "anterior down". Posterior up is based upon accurately positioning the cutting block relative to the posterior side of the distal femur (specifically, the posterior condylar surfaces as referenced by the feet of the sizing guide). Anterior down is based upon accurately positioning the cutting guide relative to the anterior side of the distal femur (specifically, the tip of the stylus). For the existing Sigma HP femoral sizing guide, the positioning of guide pins to support the cutting block (for making the anterior, posterior and chamfer cuts) is determined by coupling separate guide blocks to the femoral sizing guide.

The guide blocks and the position at which they couple to the rest of the sizing guide vary according to whether the chosen approach is posterior up or anterior down. Furthermore, the posterior up and anterior down blocks are available in four versions each which relate to different degrees of rotation of the femoral prosthesis relative to Whiteside's line or the transepicondylar axis (0°, 3°, 5° and 7° of femoral rotation). For an anterior down approach the guide blocks couple to the sizing guide close to the stylus and comprise wings which extend downwards over the transverse distal surface of the femur and include drill guides for positioning guide pins to support the selected cutting block. The guide blocks further comprises a blade which indicates alignment with Whiteside's line. For a posterior up approach the guide blocks couple to the sizing guide close to the pins securing the body to the bone, above the feet. The posterior up guide blocks comprise wings which extend over the transverse distal surface of the femur and include drill guides. The guide blocks further comprise a reference surface which indicates alignment with the transepicondylar axis.

Once the cutting block pins have been positioned, the femoral sizing guide can be removed and the appropriate cutting block (according to the selected size of femoral prosthesis) can be positioned over the guide pins to perform the anterior, posterior and chamfer cuts.

In order to position the pins to secure the cutting block for anterior down and posterior up surgical approaches, and at varying rotational positions, the existing Sigma HP femoral sizing guide comprises nine separate components. The resulting femoral sizing guide is complex and has multiple parts increasing the expense of the device and increasing the risk that an incorrect block may be used giving the wrong degree of femoral rotation or the wrong position of guide pins for the selected cutting block.

U.S. Pat. No. 6,458,135-B1 (assigned to Howmedica Osteonics Corp.) discloses a femoral sizing guide for determining the required size of femoral knee prosthesis and for determining the required location of alignment holes for securing a cutting block to the distal end of a femur. The femoral sizing guide comprises a sizing block connected to a foot component for selective pivotal movement about a pivot axis extending axially along the femur. The foot component comprises a pair of feet positioned against the posterior condylar surfaces. The centre of rotation is between the feet. A detent mechanism restricts rotational movement to predetermined angular positions. A locking mechanism is released and the device is manually turned and locked in the required position. The sizing block is positioned upon a resected transverse distal surface of the femur. Rotation of the sizing block relative to the foot component (and hence rotation of the position of the alignment holes to be drilled through the sizing block) allows the rotational position of the femoral prosthesis about the femur to be varied. The size of femoral prosthesis required can be determined either using guide structures upon the sizing block or via a stylus coupled to the sizing block.

For the Howmedica device, the position of the alignment holes is directly referenced to the posterior condylar surfaces through the selection of appropriate drill guide bushings corresponding to the selected size of femoral prosthesis coupled to the sizing block. For the Howmedica instrument set a single cutting block is used for performing an initial anterior cut, and the position of the anterior cut varies through each drill guide bushing adjusting the position of the alignment holes relative to the foot component. Further adjustment of the position of the anterior cut is provided through a sliding coupling between the sizing block and the foot component. The Howmedica femoral sizing block therefore only allows a surgeon to follow a posterior up surgical approach.

U.S. Pat. No. 7,488,324-B1 (assigned to Biomet Manufacturing Corporation) discloses a modular femoral sizing guide which facilitates the selection and orientation of a femoral knee prosthesis. A base portion is coupled to a resected transverse distal surface of the femur. An extension portion has a pair of feet to be positioned under the posterior condylar surfaces. The extension portion is rotatably coupled to the base portion. The centre of rotation is between the feet. A superstructure portion has a pair of drilling guides to prepare alignment holes extending axially into the femur to couple a cutting block to the distal femur. The superstructure further comprises a stylus to determine the required size of the femoral prosthesis.

To position the alignment holes, the Biomet femoral sizing guide comprises a first actuator to rotate the extension portion relative to the base portion (thereby rotating the drill guides about the femoral axis). The sizing guide further comprises a second actuator to adjust the height of the superstructure relative to the base portion (thereby raising or lowering the drill guides relative to the feet).

For the Biomet device, the position of the alignment holes is referenced to the stylus tip by control of the second actuator to lower the stylus and hence the drill guides until the tip of the stylus contacts the anterior cortex. Consequently, the Biomet femoral sizing block therefore only allows a surgeon to follow an anterior down surgical approach.

It is an object of embodiments of the present invention to obviate or mitigate one or more of the problems associated with the prior art, whether identified herein or elsewhere. In particular, it is an object of embodiments of the present invention to provide a femoral sizing guide for selecting a femoral prosthesis and determining the location and orientation of the prosthesis upon the distal end of the femur.

According to a first aspect of the present invention there is provided a femoral sizing guide for locating an alignment axis on a resected femoral surface at a distal end of a femur which is transverse to the longitudinal axis of the femur, the femoral sizing guide comprising: a body arranged to rest against a resected femoral surface and having first and second feet arranged to extend underneath respective posterior condyles and rest against posterior condylar surfaces of the femur; a superstructure coupled to the body and arranged to slide parallel to the resected femoral surface towards and away from the feet; and a stylus coupled to the superstructure and arranged such that when the body rests against the resected femoral surface a tip of the stylus extends over the femur such that sliding the superstructure towards the feet causes the stylus tip to contact the anterior cortex of the femur; wherein the superstructure further comprises a first guide hole defining a first alignment axis extending into the resected femoral surface at a predetermined distance from the level of the stylus tip in the plane of the resected femoral surface; and wherein the body defines a second guide hole defining a second alignment axis extending into the resected femoral surface at a predetermined distance from the feet, the distance between the first and second guide holes varying as the superstructure slides relative to the body Femoral sizing guides in accordance with the embodiments of the present invention assist a surgeon in the intraoperative selection of a femoral prosthesis and in determining the location and orientation of the prosthesis upon the distal end of the femur. Advantageously, the implanted position of the femoral prosthesis may be accurately determined relative to either the anterior cortex or the posterior cortex (specifically the posterior condylar surfaces) of the femur.

The superstructure may comprise a first pair of guide holes defining a first pair of alignment axes and the body defines a second pair of guide holes defining a second pair of alignment axes.

The first pair of alignment axes may lie in a first plane and the second pair of alignment axes may lie in a second plane such that the distance between the planes varies as the superstructure slides relative to the body.

The first and second planes may be parallel and the body may comprise a first surface arranged to bear against the resected femoral surface, wherein the alignment axes may be arranged to extend into the resected femoral surface at a predetermined angle.

The guide holes may comprise drill guides for drilling holes into the resected femoral surface or may be arranged to guide pins extending into the resected femoral surface along the alignment axes.

The body may comprise: a foot component having a first surface arranged to rest against the resected femoral surface, the foot component further comprising the first and second feet; an extension component coupled to the foot component such that the second component can rotate relative to the first component, the extension component being coupled to the superstructure such that the superstructure can slide relative to the extension component; and a locking mechanism arranged to selectively restrict or allow rotation between the first and second components; wherein the extension component defines the or each second guide hole.

The locking mechanism may comprise a lever coupled to the extension component, movement of the lever relative to the extension component being arranged to bring the lever into or out of engagement with the foot component so as to restrict or allow rotation respectively; wherein the foot component may comprise a first array of two or more grooves and the lever comprises a first tooth arranged to engage one of the first array of grooves so as to selectively restrict rotation between the foot and extension components at two or more predetermined rotational positions within a first range of rotational positions between the components; and wherein the foot component may comprise at least one further groove, the lever being arranged to engage the at least one further groove so as to selectively restrict rotation between the foot and extension components at a further predetermined rotational position within a second range of rotational positions between the components.

The foot component may further comprise at least one fixing hole arranged to receive a fixation pin to secure the foot component to a resected surface of a bone.

The extension component may be arranged to rotate relative to the foot component about an axis which extends into the resected femoral surface, the axis of rotation lying on a line which extends between the feet in the plane of the first surface of the foot component.

The superstructure may comprise a head part and first and second arms extending from the head part towards the body such that they are in sliding contact with the body, the arms defining the or each first guide hole.

The femoral sizing guide may further comprise a support rod extending from the body and received in a bore in the head part of the superstructure such that as the superstructure slides towards and away from the feet the support rod passes through the bore.

The femoral sizing guide may further comprise a locking knob coupled to the head part of the superstructure and arranged to lock the superstructure to the support rod to restrict further sliding of the superstructure relative to the body.

The stylus may comprise an elongate slot arranged to couple to the head part of the superstructure such that the stylus extends from the superstructure transverse to the support rod, the stylus slot being arranged to allow the stylus to slide relative to the support rod and to rotate about the support rod.

The stylus may comprise a first portion which extends transverse to the support rod and a second portion which is inclined relative to the first portion such that stylus tip points towards an anterior cortex of the femur.

The locking mechanism may comprise a lever coupled to the second component, movement of the lever relative to the second component being arranged to bring the lever into or out of engagement with the first component so as to selectively restrict or allow rotation between the first and second components; wherein the first component may comprise a first array of two or more grooves and the lever comprises a first tooth arranged to engage one of the first array of grooves so as to selectively restrict rotation between the first and second components at two or more predetermined rotational positions within a first range of rotational positions between the components; wherein the first component may comprise at least one further groove, the lever being arranged to engage the at least one further groove so as to selectively restrict rotation between the first and second components at a further predetermined rotational position within a second range of rotational positions between the components; and wherein the first array of two or more grooves may comprise grooves spaced apart at a first angular pitch about the centre of rotation between the first and second components and the rotational position of the at least one further groove does not correspond to the first angular pitch.

The at least one further groove may define a 0° rotational position between the components and the first array of two or more grooves define at least rotational positions which are 3°, 5° and 7° offset from the 0° rotational position.

The first range of rotational positions extends either side of the second range of rotational positions.

The first array of two or more grooves may be interrupted through the second range of rotational positions.

The lever may comprise a lever face arranged to engage the first component, the lever face comprising an array of teeth spaced apart at the first angular pitch and arranged to engage the first array of two or more grooves, the width of the lever face being less than the width of the interruption in the first array of two or more grooves through the second range of rotational positions.

One of the array of teeth on the lever face may be arranged to engage the at least one further groove to selectively restrict rotation between the first and second components at the further predetermined rotational position within the second range of rotational positions between the components.

Said one of the array of teeth may be longer than the remaining teeth such that it may engage the at least one further groove while the remaining teeth do not extend to the at least one further groove.

The extension component may be arranged to rotate relative to the foot component about an axis which extends into the resected femoral surface, the axis of rotation lying on a line which extends between the feet in the plane of the first surface of the foot component.

The second pair of guide holes may comprise guide hole sleeves extending from the extension component and through one or more arcuate slots within the foot component, the or each arcuate slot extending along a curve which has a first radius of curvature about the centre of rotation between the foot component and the extension piece such that the guide hole sleeves can slide along the or each arcuate slot.

The femoral sizing guide may further comprise a retaining bar extending between the guide hole sleeves such that the foot component is trapped between the retaining bar and the extension piece to couple the extension piece to the foot component.

The foot component may further comprise a pair of fixing holes arranged to receive a fixation pin to secure the foot component to a resected surface of a bone, the fixing holes comprising fixing hole sleeves extending from the foot component and through one or more arcuate slots within the extension component, the or each arcuate slot extending along a curve which has a second radius of curvature about the centre of rotation between the foot component and the extension piece such that the fixing hole sleeves can slide along the or each arcuate slot, the second radius of curvature being different to the first radius of curvature.

The femoral sizing guide may further comprise a spigot extending from either the foot component or the extension piece and received within an arcuate slot formed within the other of the foot component and the extension piece, the arcuate slot extending along a curve which has a third radius of curvature about the centre of rotation between the foot component and the extension piece such that the spigot can slide along the arcuate slot, the third radius of curvature being different to the first and second radii of curvature.

According to a second aspect of the present invention there is provided a method of locating an alignment axis on a resected femoral surface at a distal end of a femur which is transverse to the longitudinal axis of the femur, the method comprising: coupling a body of a femoral sizing guide to the femur such that the body rests against the resected femoral surface and first and second feet coupled to the body extend underneath respective posterior condyles and rest against posterior condylar surfaces of the femur; and sliding a superstructure coupled to the body parallel to the resected femoral surface towards the feet until a tip of a stylus coupled to the superstructure and extending over the femur contacts the anterior cortex of the femur; wherein the superstructure further comprises a first guide hole defining a first alignment axis extending into the resected femoral surface at a predetermined distance from the level of the stylus tip in the plane of the resected femoral surface and the body defines a second guide hole defining a second alignment axis extending into the resected femoral surface at a predetermined distance from the feet, the distance between the first and second guide holes varying as the superstructure slides relative to the body; and wherein the method further comprises drilling holes into the resected femoral surface through either the first or second guide holes or inserting a guide pin extending into the resected femoral surface through either the first or second guide hole along the alignment axis.

BRIEF DESCRIPTION OF THE DRAWINGS

Embodiments of the present invention will now be described, by way of example only, with reference to the accompany drawings, in which.

DETAILED DESCRIPTION OF THE INVENTION

Before a femoral sizing guide in accordance with an embodiment of the present invention can be used, the distal end of the femur must undergo initial resection to remove a distal portion of the femur to establish a surface which is transverse to the longitudinal axis of the femur. The femoral sizing guide is arranged to either allow alignment holes to be drilled into the resected surface or to place guide pins extending from the resected surface. Specifically, femoral sizing guides in accordance with embodiments of the present invention include drill guide holes which allow either holes to be drilled into the resected surface of the bone or guide pins to be directly inserted into the bone passing through the drill guides. The alignment holes or guide pins are used to position a cutting block upon the surface of the bone to perform the shaping resections of the end of the femur. Consequently, the position of the alignment holes/guide pins determined by drill guides on the femoral sizing guide relative the condyles/anterior cortex and their rotational position about the axis of the femur determine the final implanted position of the femoral prosthesis.

As noted above in connection with the known Sigma HP femoral sizing guide, there are two principal options for positioning a cutting block to prepare a distal end of a femur to receive a femoral knee prosthesis: anterior down and posterior up. The choice is dependent partially upon surgeon preference. An anterior down approach prevents notching of the anterior cortex of the distal femur or the femoral prosthesis overhanging at the expense of less control over the position of the prosthetic posterior condyles. A posterior up approach allows accurate control of the position of the posterior condyles and therefore better control of the joint tension when the knee is in flexion. The femoral prostheses may be provided in a range of sizes with regular size increments. For instance, the femoral prostheses may be provided in increments of 3 mm, though it will be appreciated that other increments are possible. Femoral sizing guides in accordance with embodiments of the present invention are required to locate guide holes or pins extending into the resected surface at a constant position relative to either the anterior cortex or the posterior condyles irrespective of the selected size of the femoral prosthesis. The stylus provides a guide to the appropriate size implant and, therefore, cutting block to use. As the position of the guide pins is selected using the femoral sizing guide, the cutting blocks can be designed to have a fixed distance between the pin holes and the position of the bone cut, rather than requiring that the cutting blocks allow the position of the bone cut to be adjusted relative to the pin positions. The cutting block may provide further adjustment means allowing the surgeon to control the position of the cutting block relative to the anterior cortex or posterior condyles. For an exemplary range of femoral prosthesis having 3 mm size increments, the cutting blocks may be arranged to allow the position of each cutting block relative to the guide pin or guide holes (and therefore relative to the anterior cortex or posterior condyles) to within + or −1.5 mm. This allows for flexibility to accommodate femurs which fall between standard sizes of the femoral prosthesis. The cutting block adjustment means may comprise a series of three holes to receive each guide pin. A first hole is at the normal position and the other holes are 1.5 mm above and below the first hole.

Figure 1:
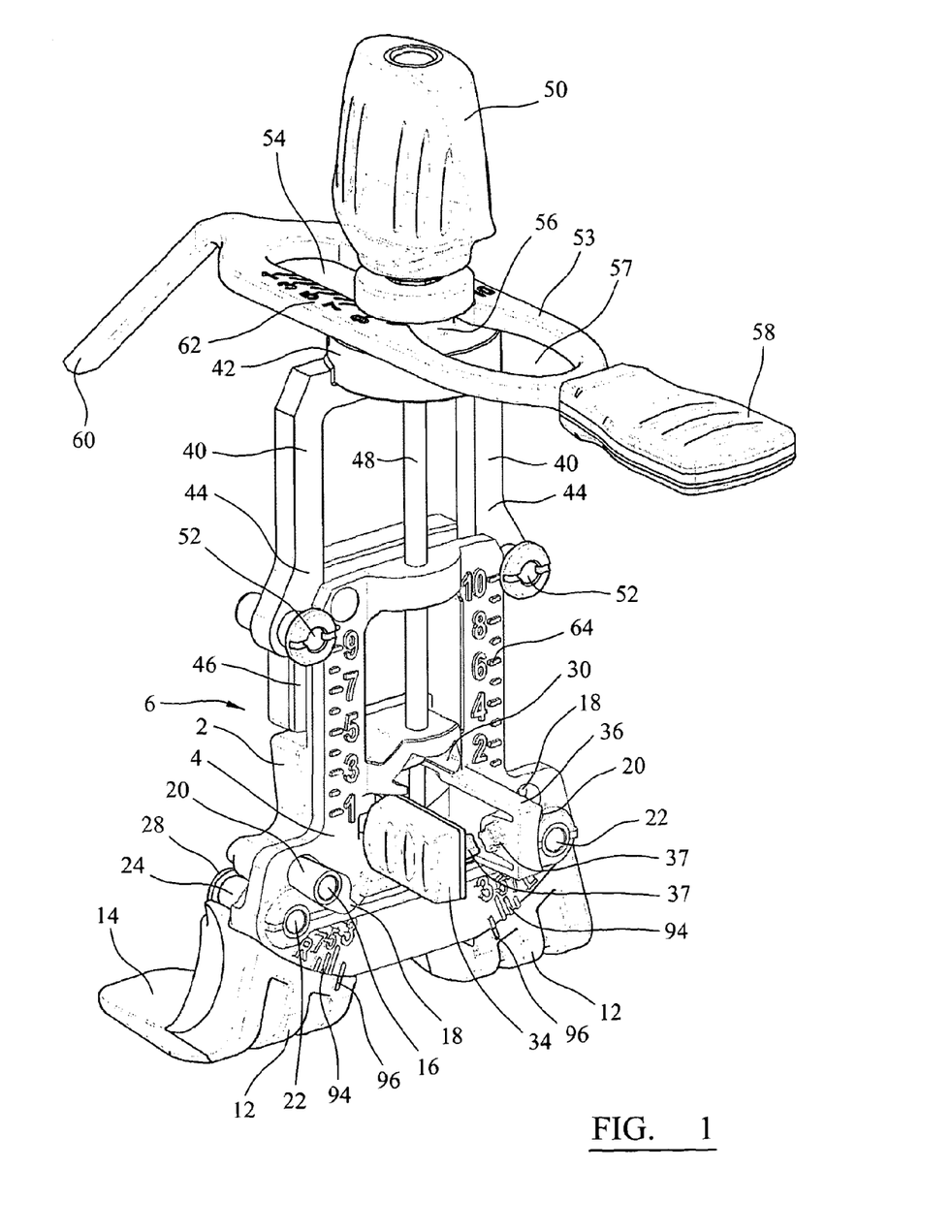
FIGS. 1 and 2 illustrate first and second views of a femoral sizing guide in accordance with an embodiment of the present invention from different perspectives.
Figure 2:
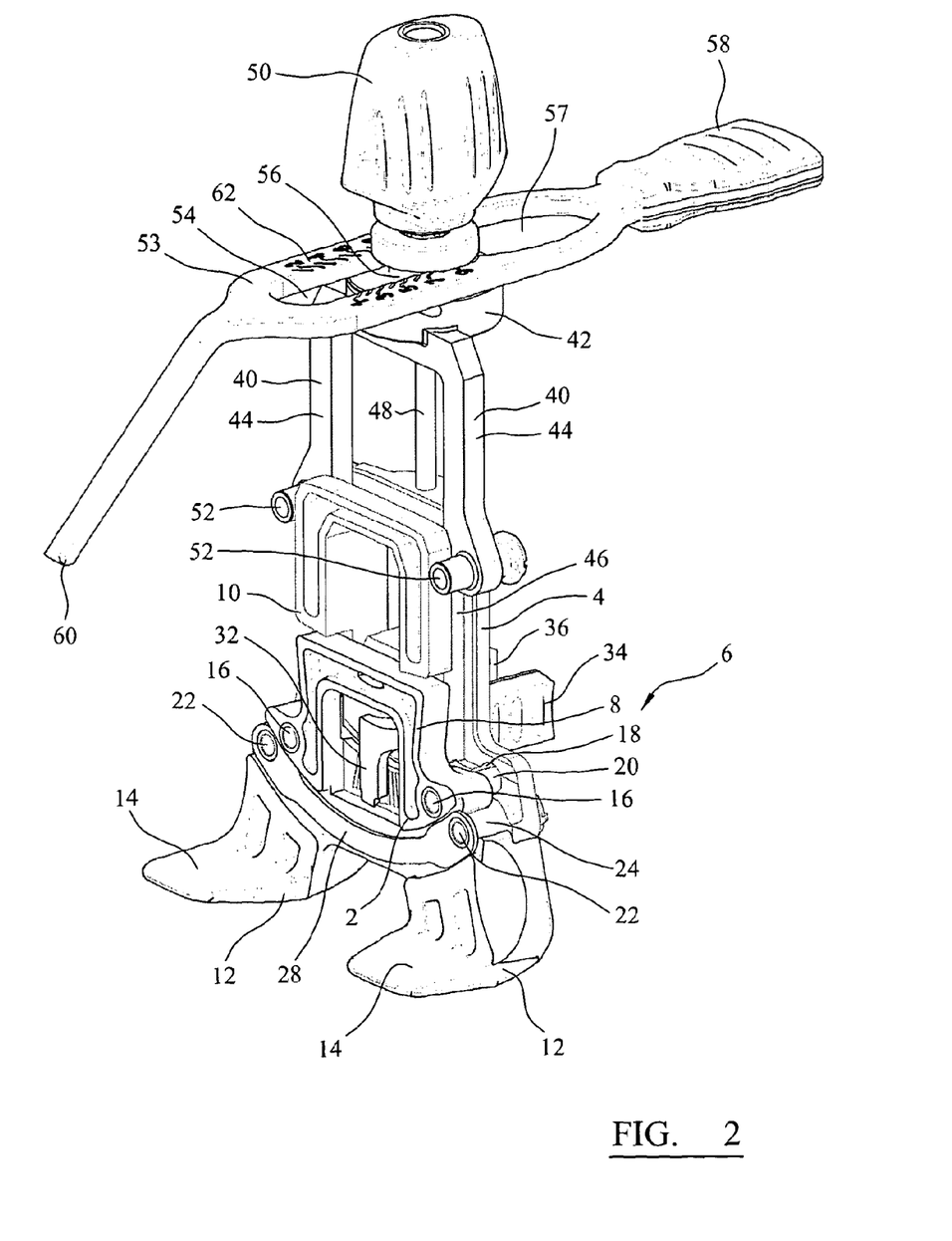
Figure 3:
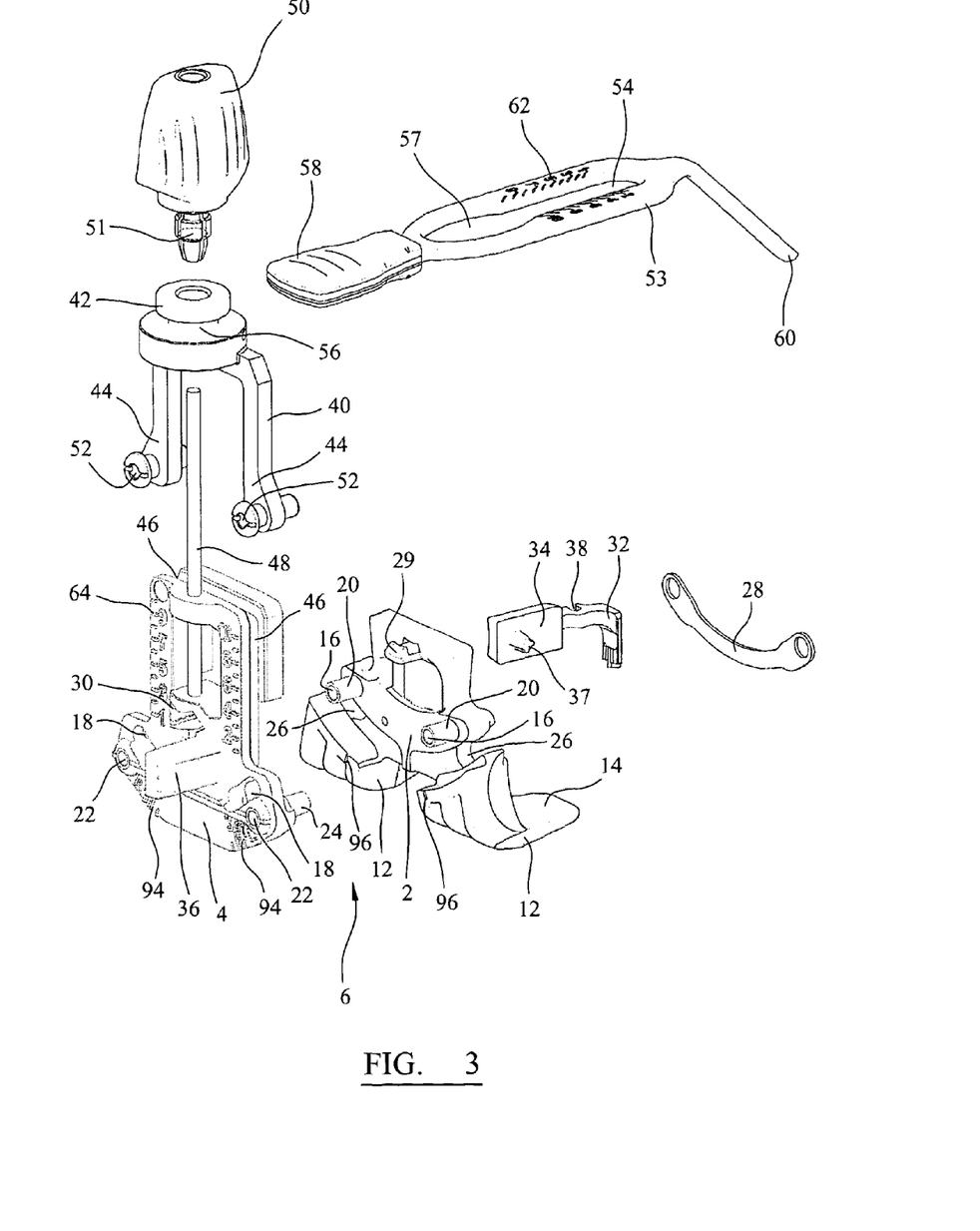
FIGS. 3 and 4 illustrate exploded views of the femoral sizing guide of FIGS. 1 and 2 from different perspectives.
Figure 4:
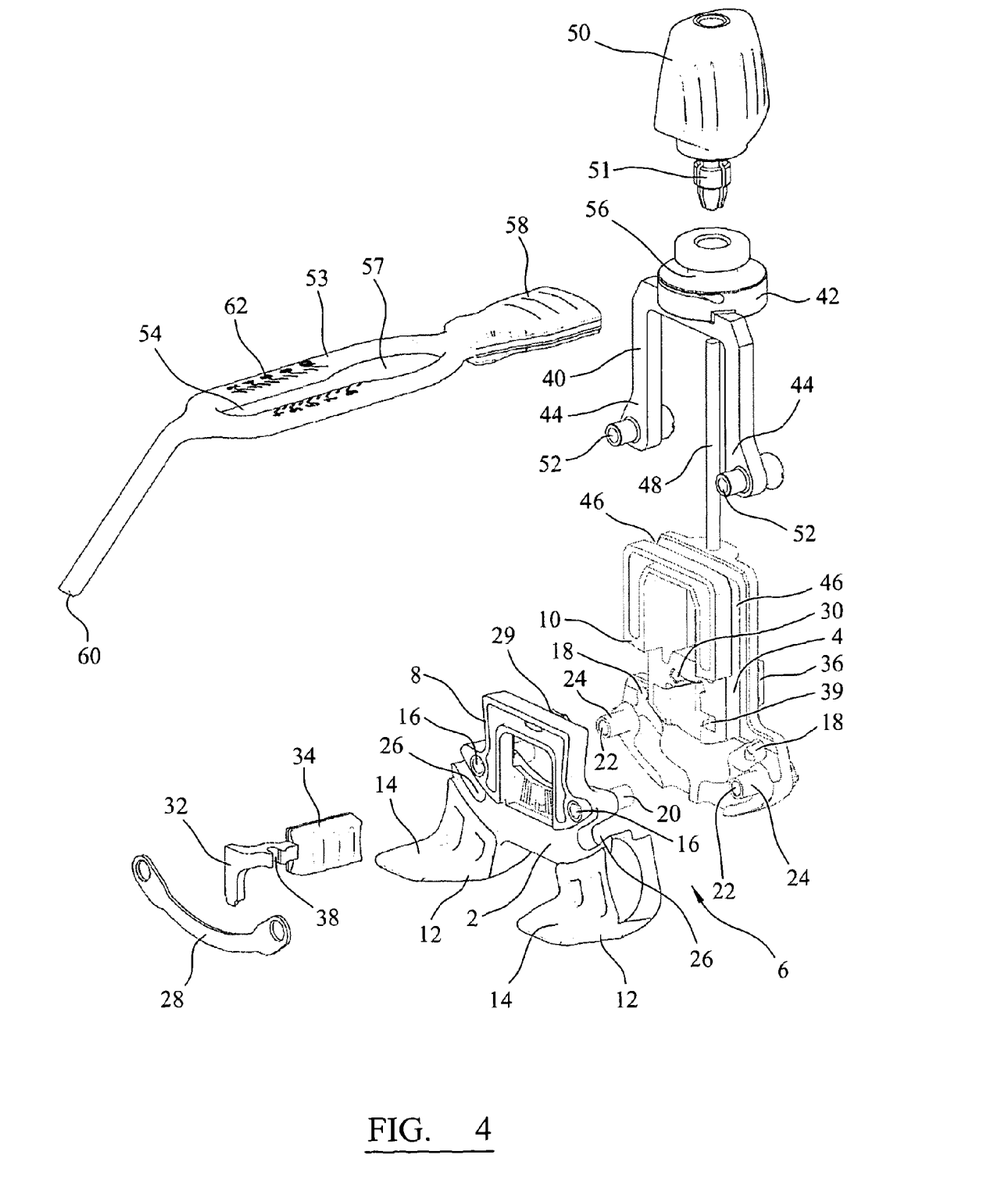

FIGS. 1 and 2 illustrate perspective views of a femoral sizing guide in accordance with an embodiment of the present invention. FIGS. 3 and 4 illustrate exploded views. The femoral sizing guide comprises a foot component 2 and an extension piece 4, collectively forming a body 6. The foot component 2 and the extension piece 4 are rotatably coupled together as will be described in greater detail below. The foot component 2 comprises a first side 8 (visible in FIGS. 2 and 4) which in use is placed against the resected distal surface of the femur. Similarly the extension piece 4 also has a first surface 10 (visible in FIGS. 2 and 4) to bear against the femur. The foot component 2 comprises first and second feet 12 which in use extend underneath the posterior condyles. In particular, foot locator surfaces 14 are arranged to bear against respective posterior condylar surfaces to locate the femoral sizing guide on the resected femoral surface. The foot component 2 further comprises first and second pin holes 16. When the femoral sizing guide is correctly positioned on the resected femoral surface, such that the foot locator surfaces bear against respective posterior condylar surfaces, fixing pins are driven into the resected bone surface through pin holes 16 to secure the femoral sizing guide in place to prevent further movement of the foot component 2 relative to the femur.

The extension piece 4 is rotatably coupled to the foot component 2 such that when the foot component 2 is pinned to the femur the extension piece can rotate by sliding over the bone surface. The centre of rotation is generally positioned between the feet 12 such that when the femoral sizing guide is pinned to the bone the centre of rotation is generally aligned with Whiteside's line. However, there is no pivotal connection at the centre of rotation. Advantageously, this allows the surgeon a clear view of Whiteside's line, which assists with determining the required rotational alignment of the femoral prosthesis. The extension piece 4 comprises first and second arcuate grooves 18 which are defined by a curve radiating from the centre of rotation of the foot component 2 and the extension piece 4. Each groove 18 is arranged to receive an extended sleeve portion 20 of a foot component pin hole 16 such that as the extension piece 4 rotates relative to the foot component 2 its movement is constrained by the pin holes sleeves 20 sliding through grooves 18. The range of rotational movement of the extension piece 4 relative to the foot component 2 is limited by the pin hole sleeves 20 bearing against closed outer ends of the arcuate grooves 18.

The extension piece 4 further comprises a first pair of guide holes 22 for determining the axes of alignment holes or guide pins extending into the resected femur for a posterior up approach, as will be described in greater detail below. The guide holes 22 comprise sleeve portions 24 which extend through arcuate grooves 26 formed in the foot component 2. The foot component slots 26 are open ended as they extend to the edge of the foot component 2 and are defined by a curve having a larger radius of curvature than the radius of curvature for the extension piece slots 18. Slots 18 and 26 extend about the same centre of curvature. As the extension piece 4 rotates relative to the foot component 2 the guide hole sleeves 24 slide along foot component grooves 26. The range of rotational movement of the extension piece 4 relative to the foot component 2 is further limited by the guide hole sleeves 24 bearing against the closed ends of foot component grooves 26.

To secure the extension piece 4 to the foot component 2 a retaining bar 28 extends between the guide hole sleeves 24 such that the foot component 2 is sandwiched between the extension piece 4 and the retaining bar 28. To provide further stability to the assembled femoral sizing guide, a spigot 29 (not visible in FIGS. 1 and 2) extends from the foot component 2 into an arcuate slot 30 formed in the extension piece 4 such that the spigot 29 slides within slot 30 as the extension piece rotates relative to the foot component 2. The arcuate slot 30 is defined by a curve radiating from the centre of rotation between the foot component 2 and the extension piece 4.

A locking mechanism is provided to lock the extension piece 4 to the foot component 2 at predetermined rotational positions. The locking mechanism comprises a lever 32 which is pivotally coupled to the extension piece 4. The lever 32 is operated by trigger 34, specifically by squeezing trigger 34 against bar 36 which extends outwardly from the extension piece 4. The lever 32 is biased towards the foot component 2 by a spring (not illustrated) which extends between lugs 37 formed on the trigger 34 and the bar 36 such that when the trigger 34 is released the lever bears against the foot component 2 to prevent further rotation of the extension piece. The lever 32 comprises a groove 38 which couples to a bar 39 formed within the extension piece 4 to allow the lever to rotate relative to the extension piece 4. It will be appreciated that alternative mechanisms for coupling the lever 32 to the extension piece 4 are possible, the only requirement being that relative movement between the lever 32 and the foot component 2 is provided to allowing locking and unlocking. For instance, a pin may be provided press fitted into a hole formed in lever 32 generally at the position of groove 38. The pin may be received and rotate within a hole in extension piece 4. The locking mechanism is described in greater detail below.

The femoral sizing guide further comprises a superstructure 40 which is coupled to the extension piece 4 and arranged to slide relative to the extension piece 4 generally towards and away from the feet 12. The superstructure 40 comprises a head part 42 and arms 44 which extend downwardly and are arranged to slide within channels 46 formed in the sides of the extension piece 4. A support rod 48 extends upwards from the central part of the extension piece 4 and passes through the superstructure head 42. The support rod 48, together with arms 44 sliding in channels 46 serve to control sliding movement of the superstructure 40 and to prevent twisting of the superstructure 40 relative to the extension piece 4 as it slides. The superstructure 40 can be locked in position relative to the extension piece 4 by tightening locking knob 50, which compresses a collet 51 (visible in FIGS. 3 and 4) over the support rod 48.

The superstructure 40 further comprises a second pair of guide holes 52 positioned towards the free ends of the arms 44. The second pair of guide holes 52 is for determining the axes of alignment holes extending into the resected femur for an anterior down approach, as will be described in greater detail below. Superstructure guide holes 52 are used as an alternative to the extension piece guide holes 22, as will be described below as part of the surgical technique for using the femoral sizing guide. The superstructure guide holes 52 comprise sleeves such that in use the tips of the sleeves are contact with the resected bone surface.

The femoral sizing guide further comprises a stylus 53 coupled to the head part 42 of the superstructure 40. The stylus 53 is arranged to extend over the distal end of the femur when the femoral sizing guide is coupled to the resected distal surface of the femur. The stylus 53 is coupled to the superstructure 40 such that it extends from head part 42 substantially at 90° to the axis of support rod 48. The stylus 53 comprises an elongate slot 54 arranged to engage a neck 56 of the head part 42 so that the stylus can slide relative to the head part 42 and can rotate about the body part 42. The stylus slot 54 further comprises an enlarged portion 57 arranged to pass over the upper side of head part 42 and the locking knob 50 to detach the stylus 53 from the femoral sizing guide. The stylus 53 further comprises a handle 58 at a first end to rotate the stylus 53 relative to the superstructure 40 and to slide the slot 54 over the neck 56 of the superstructure 40.

At the second end, the stylus 53 is bent downwards towards a stylus tip 60. The stylus tip 60 is arranged to contact the anterior cortex of the femur by sliding and rotating the stylus 53 relative to the superstructure 40 and by sliding the superstructure 40 relative to the extension piece 4. The stylus 53 has a scale 62 marked along both sides of slot 54. Each mark on the scale 62 corresponds to a selected size of femoral prosthesis. The position of the stylus is indicated by the mark on the stylus scale 62 adjacent to head part 42 on the stylus handle side of the body part 42. Similarly, the extension piece 4 further comprises a scale 64 marked along both sides of the extension piece 4. Each mark on the extension piece scale 64 corresponds to a selected size of femoral prosthesis. The position of the superstructure 40 relative to the extension piece 4 is indicated by the mark on the superstructure scale 64 adjacent to the centre of the superstructure guide holes 52. Stylus scale 62 and superstructure scale 64 both indicate the same range of sizes of femoral prosthesis. When the superstructure 40 and the stylus 53 are both positioned at corresponding locations on scales 64, 62 then the stylus tip 60 indicates the exit point on the anterior cortex for the selected size of femoral prosthesis. Both the superstructure 40 and the stylus 53 are adjusted according to their respective scales until the stylus tip 60 is just in contact with the anterior cortex of the bone as the stylus tip 60 is swept across the anterior cortex. The scales 62, 64 then indicate the required size of femoral prosthesis, as will be described in greater detail below in connection with the remainder of the surgical technique for using the femoral sizing guide.

Figure 5A:
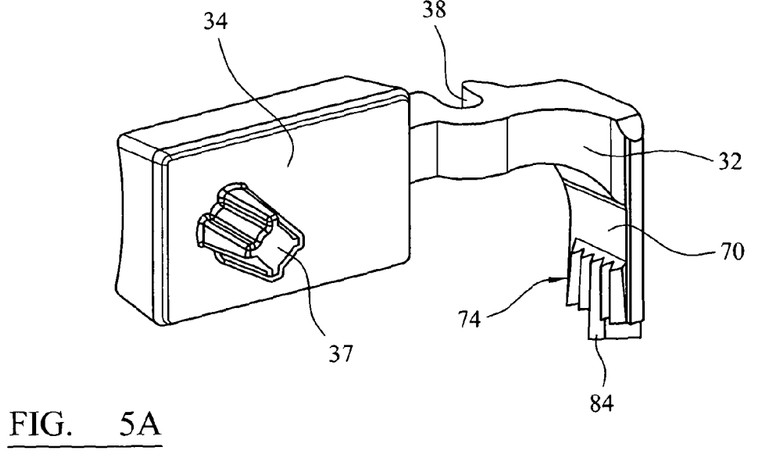
FIGS. 5A and 5B illustrate enlarged views of parts of the locking mechanism of the femoral sizing guide of FIGS. 1 and 2.
Figure 5B:
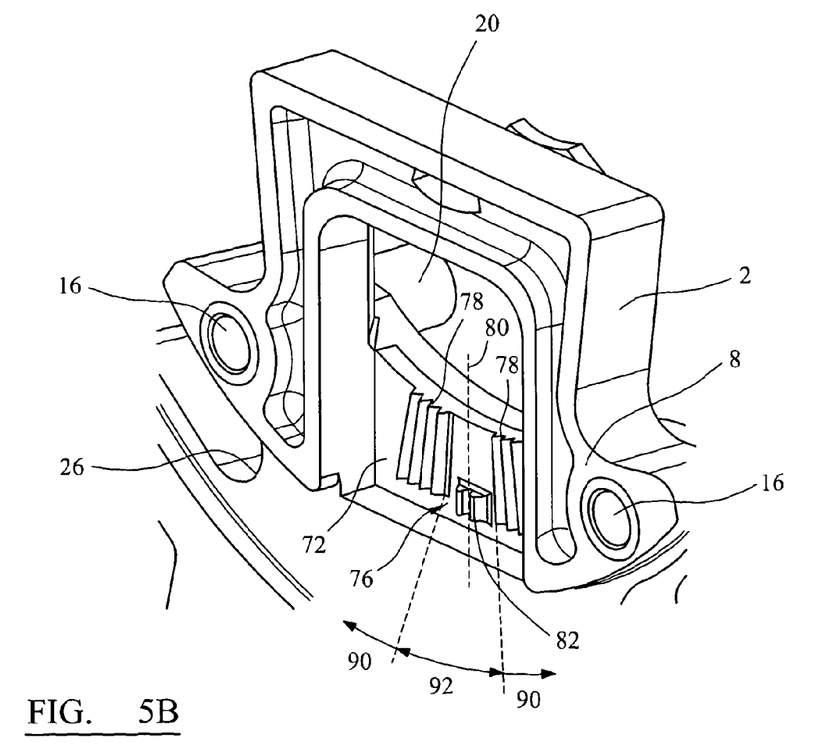

Referring now to FIGS. 5A and 5B these illustrate enlarged portions of the sizing guide locking mechanism in order that the operation of the locking mechanism may be more clearly understood. FIG. 5A illustrates lever 32 separated from the extension piece 4. Lever 32 is illustrated from the same perspective as the exploded view of FIG. 3. FIG. 5B illustrates part of the foot component 2 separated from the extension piece 4. The foot component 2 is illustrated from the same perspective as the exploded view of FIG. 4. The lever 32 of FIG. 5A and the foot component of FIG. 5B are viewed from different perspectives so as to allow the portions of each component that face one another to be viewed.

As noted above, the lever 32 is coupled to the extension piece 4 such that it can rotate into and out of contact with the foot component 2 to lock the rotational position of the extension piece 4 relative to the foot component 2. The lever 32 is biased towards the foot component 2, but the bias can be overcome by the surgeon squeezing trigger 34 towards bar 36. The lever 32 has a lever face 70 which bears against a ratchet plate 72 on the foot component 2. The lever face 70 has an array of teeth 74 which bear against a curved ratchet 76 on the ratchet face 72. When the trigger 34 is squeezed against bar 36 teeth 74 are disengaged from the curved ratchet 76. The extension piece 4 can be freely rotated relative to the foot component 2 within a predetermined rotational range limited by movement of sleeves 20 and 24 within respective slots 18 and 26.

When the trigger 34 is released, the teeth 74 engage the curved ratchet 76 causing the orientation of the extension piece 4 relative to the foot component 2 to be limited to a series of predetermined rotational positions. For instance, the locking mechanism may be arranged to allow the extension piece 4 to be locked relative to the foot component 2 at 0° (which corresponds to a symmetrically upright position). As the extension piece 4 rotates relative to the foot component 2 the vertical rod 48 also rotates. Rod 48 serves as a visual reference to the correct rotational position of the extension piece. The correct rotational position of the extension piece 4 relative to the foot component 2 is indicated when rod 48 is aligned with Whiteside's line, which generally corresponds to an anterior to posterior axis for the distal femur. Additionally, horizontal lines formed in the visible end of guide sleeves 52 serve as a visual reference for aligning the rotation of the extension piece relative to the transepicondylar axis. Rotation of the extension piece 4 relative to the foot component 2 may be locked at +/−3°, 5° and 7° relative to the 0° position. While the locking mechanism is released the extension piece 4 may be freely rotated until the rod 48 is brought into alignment with Whiteside's line. The locking mechanism may then be engaged. The interaction of the teeth 74 with the curved ratchet 76 serves to cause the position of the extension piece 4 relative to the foot component 2 to settle at the closest position. Advantageously, although the locking mechanism is small, it still allows accurate selection of 0° and +/−3°, 5° or 7° of offsets. This selection is achieved by having two sets of grooves within the curved ratchet 76. An upper ratchet 78 has a 2° pitch and is provided in two separate portions with a space in between. Each portion of the upper ratchet 78 is aligned with +/−3°, 5° or 7° grooves relative to a centreline 80. The grooves in the upper ratchet 78 are arranged to engage corresponding teeth 74 on the lever face 70. Consequently, the upper ratchet 76 allows the orientation of the extension piece 4 relative to the foot component 2 to be fixed at predetermined positions (+/−3°, 5° or 7°) within first portions of the predetermined rotational range indicated by arrows 90.

The curved ratchet 76 further comprises a second, lower ratchet 82 which comprises a single groove aligned with the 0° position. It will be appreciated that the second ratchet 82 may overlap with the first ratchet 78, as illustrated in FIG. 5B so long as there is a sufficient difference in alignment so allow the first ratchet to be engaged without interference from the second ratchet, and vice versa, as will now be described. The lever teeth 74 have an elongated central tooth 84 which is arranged to engage lower ratchet groove 82 when the lever is centrally positioned across curved ratchet 76. There is only a single groove 84 within a second, central portion of the predetermined rotational range of the extension piece 4 relative to the foot component 2 indicated by arrow 92. Consequently, the extension piece 4 can only be locked relative to the foot component at a single position within the second portion 92 of the predetermined rotational range. It will be appreciated that in alternative embodiments of the invention there may be more than two separation portions of the predetermined rotational range, each supporting ratchets which are arranged to be separately engaged by the lever 32 to allow the extension piece to be locked relative to the foot component. Furthermore, within each portion of the rotational range the corresponding ratchet may be arranged to allow the orientation of the extension piece relative to the foot component to be locked at one or more predetermined orientations, according to the number of grooves. Groove 82 has broad shoulders preventing the central lever tooth 84 from settling at other positions within the second portion 92 of the rotational range. The upper ratchet 78 has a gap in the second portion 92 of the rotational range. This prevents the remainder of the lever teeth from clashing with the upper ratchet. As the central lever tooth 84 comprises an extension of tooth at the same pitch as the remainder of the lever teeth 74 when the lever engages the upper ratchet in the first portions of the rotational range the central tooth 84 meshes with the upper ratchet 76.

It will be appreciated that because the upper ratchet 78 has a 2° pitch at positions +/−3°, 5° or 7°, it would not be possible for this ratchet to accommodate a 0° position. The provision of a separate ratchet comprising one or more grooves centred on 0° which is engaged by one or more extended teeth allows the 0° position also to be selected. It will be appreciated that alternatively a single ratchet could be provided with teeth having a 1° pitch. However, a ratchet with 1° teeth would either have very small teeth not able to securely lock the extension piece 4 to the foot component 2 or would have to extend over a large area. The arrangement of two separate ratchets which are separately engaged overcomes these problems. It will be appreciated that there are other mechanisms by which this effect could be achieved. For instance, the central groove 82 may be omitted and the whole of the lever face 70 including all of the teeth 74 may be arranged to be received in the gap in the centre of the upper ratchet 76 to lock the mechanism at the 0° position. That is, the whole of the gap in the upper ratchet 76 may comprise at least one further groove. Other arrangements will be apparent to the appropriately skilled person in which a lever may engage a ratchet having first regular pitch at a position not corresponding to the ratchet pitch.

Figure 6:
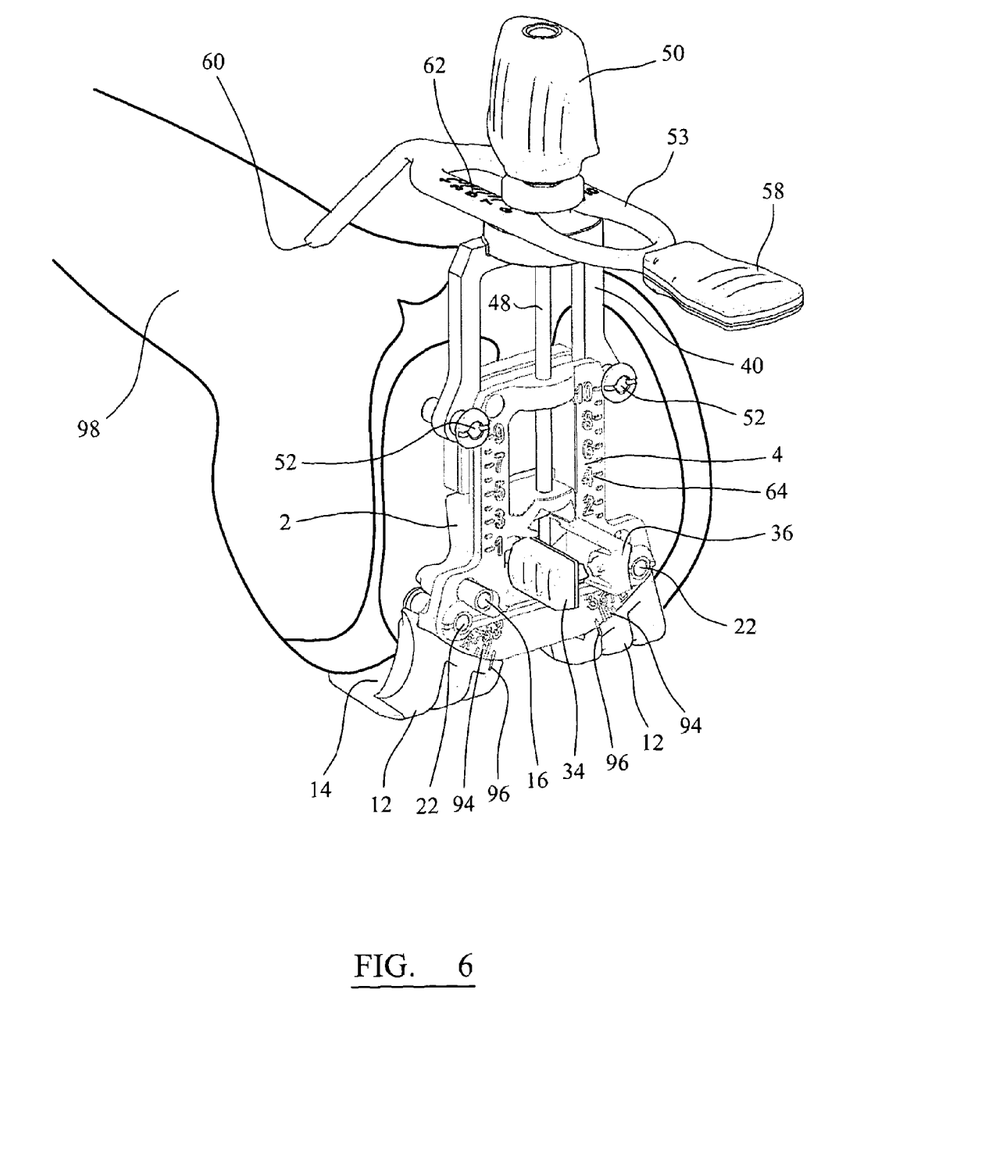
FIG. 6 illustrates the femoral sizing guide of FIG. 1 coupled to a resected surface at the end of a femur.

A method of using a femoral sizing guide in accordance with an embodiment of the present invention will now be described in connection with FIG. 6 which illustrates the femoral sizing guide coupled to a resected distal portion of the bone. A foot component 2 is positioned against the end of the bone such that surface 8 is in contact with the bone and the feet 12 extend under the posterior condyles. The foot component is then moved across the resected surface until the foot locator surfaces 14 bear against the posterior condylar surfaces (that is, the femoral sizing guide is centrally located on the end of the bone. The femoral sizing guide can then be secured to the bone by passing fixing pins through holes 16 in the foot component into the bone.

The rotational alignment of the extension piece (and hence the rotational alignment of the guide pins for securing the cutting block and the resulting femoral prosthesis) can then be set. The required rotational alignment may be determined during pre-operative planning or intra-operatively using anatomical landmarks, for instance by rotating the extension piece 4 relative to the foot component 2 until the rod 48 is aligned with Whiteside's Line. The rotation is set by squeezing the trigger 34 and bar 36 together to release the locking mechanism and then manually rotating the extension piece 4 and superstructure 40. When the required rotation is set and checked on scale 94 on the extension piece relative to a mark 96 on the foot component, the locking mechanism is engaged by releasing trigger 34.

As discussed above, the sizing guide can be set to varying sizes of femoral prosthesis by adjusting the height of the superstructure 40 relative to scale 64 on the extension piece 4. The superstructure 40 is raised and lowered by releasing and tightening locking knob 50 to cause collet 51 to grip or release the rod 48. Additionally, the position of the stylus 53 is set by sliding stylus slot 54 over extension piece neck 56 and reading the stylus position on scale 62. For each femoral prosthesis selected for the stylus on scale 62, the superstructure should be set to the same size on scale 64. The tip 60 of the stylus is positioned on the anterior cortex of the femur at the position the surgeon has chosen for the anterior cut to exit the bone. The selected size of femoral prosthesis on scale 62 is then transferred to scale 64 by sliding the superstructure 40 relative to the extension piece 4. Ideally for the chosen prosthesis size the stylus tip should just touch the anterior cortex; however in practice the stylus tip may touch the anterior cortex at a position where the indication of prosthesis size by the position of the superstructure 40 relative to the extension piece 4 is between two standard sizes of prosthesis. Whether the next largest or next smallest prosthesis is chosen is at the choice of the surgeon.

Guide pins to support the cutting block can then be inserted through either the lower alignment holes 22 (for a posterior up approach) or the upper alignment holes 52 (for an anterior down approach). The choice between anterior down and posterior up approaches is the same as for the Sigma HP instrument set described above. Either guide pins are inserted into the bone through the alignment holes or alignment holes may be drilled into the bone. The sizing guide is then removed and the guide pins or holes used to mount a cutting guide to perform the shaping resections for the selected size of femoral prosthesis.

It will be readily apparent to the appropriately skilled person that further modifications may be made to the present invention and further applications may be found for the present invention from the teaching herein, without departing from the scope of the appended claims.

The invention claimed is:

1. A femoral sizing guide for locating an alignment axis on a planar resected femoral surface at a distal end of a femur that is transverse to the longitudinal axis of the femur, the distal end of the femur having an anterior cortex, the femoral sizing guide comprising:
   a body comprising:
      a foot component having a first surface arranged to rest against the resected femoral surface, the foot component further comprising first and second feet arranged to extend underneath respective posterior condyles and rest against posterior condylar surfaces of the femur;
      an extension component coupled to the foot component such that the extension component can rotate relative to both feet of the foot component; and
      a locking mechanism arranged to selectively restrict rotation between the foot component and the extension component;
      a superstructure slidably coupled to the extension component in a direction substantially parallel to the resected femoral surface; and
      a stylus coupled to the superstructure and arranged such that when the body rests against the resected femoral surface a tip of the stylus extends over the femur such that sliding the superstructure towards the feet causes the stylus tip to contact the anterior cortex of the femur at a level;
   wherein the superstructure further comprises a first set of spaced guide holes defining a first alignment axis at a predetermined distance from the level of the stylus tip in the plane of the resected femoral surface;
   wherein the extension component includes a pair of spaced sleeves that define a second set of guide holes defining a second alignment axis, the distance between the first and second sets of guide holes varying as the superstructure slides relative to the body;
   wherein portions of the sleeves of the extension component extend into spaced arcuate grooves in the foot component, the spaced arcuate grooves defining arcuate paths; and
   wherein portions of the sleeves of the extension component move along the arcuate paths defined by the arcuate grooves in the foot component when the extension component rotates with respect to the feet of the foot component.

2. The femoral sizing guide of claim 1, wherein the first alignment axis lies in a first plane and the second alignment axis lies in a second plane such that the distance between the planes varies as the superstructure slides relative to the body.

3. The femoral sizing guide of claim 2, wherein the first and second planes are parallel and the body comprises a first surface arranged to bear against the resected femoral surface, wherein the alignment axes are arranged to extend into the resected femoral surface at a predetermined angle.

4. The femoral sizing guide of claim 1, wherein the guide holes comprise drill guides for drilling holes into the resected femoral surface or are arranged to guide pins extending into the resected femoral surface along the alignment axes.

5. The femoral sizing guide of claim 1, wherein the locking mechanism comprises a lever coupled to the extension component, movement of the lever relative to the extension component being arranged to bring the lever into or out of engagement with the foot component so as to restrict or allow rotation respectively;

wherein the foot component has a first array of two or more grooves and the lever comprises a first tooth arranged to engage one of the first array of grooves so as to selectively restrict rotation between the foot and extension components at two or more predetermined rotational positions within a first range of rotational positions between the components; and wherein the foot component has at least one further groove, the lever being arranged to engage the at least one further groove so as to selectively restrict rotation between the foot and extension components at a further predetermined rotational position within a second range of rotational positions between the components.

6. The femoral sizing guide of claim 5, wherein the foot component has at least one fixing hole arranged to receive a fixation pin to secure the foot component to a resected surface of a bone.

7. The femoral sizing guide of claim 6, wherein the extension component is arranged to rotate relative to the foot component about an axis that extends into the resected femoral surface, the axis of rotation lying on a line that extends between the feet in the plane of the first surface of the foot component.

8. The femoral sizing guide of claim 1, wherein the superstructure comprises a head part, and first and second arms extending from the head part towards the body such that they are in sliding contact with the body, the arms defining the first pair of guide holes.

9. The femoral sizing guide of claim 8, further comprising a support rod extending from the body and received in a bore in the head part of the superstructure such that as the superstructure slides towards and away from the feet, the support rod passes through the bore.

10. The femoral sizing guide of claim 9, further comprising a locking knob coupled to the head part of the superstructure and arranged to lock the superstructure to the support rod to restrict further sliding of the superstructure relative to the body.

11. The femoral sizing guide of claim 9, wherein the stylus has an elongate stylus slot arranged to couple to the head part of the superstructure such that the stylus extends from the superstructure transverse to the support rod, the stylus slot being arranged to allow the stylus to slide relative to the support rod and to rotate about the support rod.

12. The femoral sizing guide of claim 11, wherein the stylus comprises a first portion that extends transverse to the support rod and a second portion that is inclined relative to the first portion such that stylus tip points towards an anterior cortex of the femur.

13. The femoral sizing guide of claim 1 wherein:
the foot component includes a pair of spaced sleeves that defines spaced guide holes; and
portions of the sleeves of the foot component extend into spaced arcuate grooves in the extension component.

14. The femoral sizing guide of claim 1 wherein the arcuate grooves in the foot component have a common center of curvature.

15. The femoral sizing guide of claim 14 wherein:
the spaced arcuate grooves in the extension component have a common center of curvature with the arcuate grooves in the foot component; and
portions of the sleeves of the foot component move along arcuate paths defined by the arcuate grooves in the extension component when the extension component rotates with respect to the feet of the foot component.

16. The femoral sizing guide of claim 15 further comprising a retaining bar that extends between the sleeves of the extension component such that a portion of the foot component is sandwiched between the extension component and the retaining bar.

17. A femoral sizing guide for locating an alignment axis on a planar resected femoral surface at a distal end of a femur that is transverse to the longitudinal axis of the femur, the distal end of the femur having an anterior cortex, the femoral sizing guide comprising:
a body comprising:
a foot component having a first surface arranged to rest against the resected femoral surface, the foot component further comprising first and second feet arranged to extend underneath respective posterior condyles and rest against posterior condylar surfaces of the femur and a pair of spaced sleeves that define spaced guide holes;
an extension component coupled to the foot component such that the extension component can rotate relative to both feet of the foot component; and
a locking mechanism arranged to selectively restrict rotation between the foot component and the extension component;
a superstructure slidably coupled to the extension component in a direction substantially parallel to the resected femoral surface; and
a stylus coupled to the superstructure and arranged such that when the body rests against the resected femoral surface a tip of the stylus extends over the femur such that sliding the superstructure towards the feet causes the stylus tip to contact the anterior cortex of the femur at a level;
wherein the superstructure further comprises a first set of spaced guide holes defining a first alignment axis at a predetermined distance from the level of the stylus tip in the plane of the resected femoral surface;
wherein the extension component includes a second set of guide holes defining a second alignment axis, the distance between the first and second sets of guide holes varying as the superstructure slides relative to the body;
wherein portions of the sleeves of the foot component extend into spaced arcuate grooves in the extension component, the spaced arcuate grooves defining arcuate paths; and
wherein portions of the sleeves of the foot component move along the arcuate paths defined by the arcuate grooves in the extension component when the extension component rotates with respect to the feet of the foot component.

18. A femoral sizing guide for locating an alignment axis on a planar resected femoral surface at a distal end of a femur that is transverse to the longitudinal axis of the femur, the distal end of the femur having an anterior cortex, the femoral sizing guide comprising:
a body comprising:
a foot component having a first surface arranged to rest against the resected femoral surface, the foot component further comprising first and second feet arranged to extend underneath respective posterior condyles and rest against posterior condylar surfaces of the femur and a pair of spaced sleeves that define spaced guide holes;
an extension component coupled to the foot component such that the extension component can rotate relative to both feet of the foot component; and
a locking mechanism arranged to selectively restrict rotation between the foot component and the extension component;

a superstructure slidably coupled to the extension component in a direction substantially parallel to the resected femoral surface; and a stylus coupled to the superstructure and arranged such that when the body rests against the resected femoral surface a tip of the stylus extends over the femur such that sliding the superstructure towards the feet causes the stylus tip to contact the anterior cortex of the femur at a level;

wherein the superstructure further comprises a first set of spaced guide holes defining a first alignment axis at a predetermined distance from the level of the stylus tip in the plane of the resected femoral surface;

wherein the extension component includes a second set of guide holes defining a second alignment axis, the distance between the first and second sets of guide holes varying as the superstructure slides relative to the body;

wherein portions of the sleeves of the extension component extend into spaced arcuate grooves in the foot component, the spaced arcuate grooves defining arcuate paths; and wherein portions of the sleeves of the extension component move along the arcuate paths defined by the arcuate grooves in the foot component when the extension component rotates with respect to the feet of the foot component;

wherein portions of the sleeves of the foot component extend into spaced arcuate grooves in the extension component, the spaced arcuate grooves defining arcuate paths; and wherein portions of the sleeves of the foot component move along the arcuate paths defined by the arcuate grooves in the extension component when the extension component rotates with respect to the feet of the foot component.

* * * * *